United States Patent
Bartholomew et al.

(10) Patent No.: US 6,415,235 B1
(45) Date of Patent: Jul. 2, 2002

(54) FIXED OPTIC SENSOR SYSTEM AND DISTRIBUTED SENSOR NETWORK

(75) Inventors: Dwight U. Bartholomew, Dallas; Jose L. Melendez, Plano; Richard A. Carr, Rowlett, all of TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 08/959,949

(22) Filed: Oct. 29, 1997

Related U.S. Application Data

(60) Provisional application No. 60/029,976, filed on Nov. 6, 1996.

(51) Int. Cl.[7] ............................................... G01N 21/55
(52) U.S. Cl. .............................. 702/28; 702/22; 702/30; 702/32; 356/445
(58) Field of Search ............................... 702/28, 31, 32, 702/188, 134, 130, 19, 22, 27, 80, 85, 159, 172, 183, FOR 103, FOR 104, FOR 131, FOR 115–119, FOR 134, FOR 135, FOR 156–FOR 163, FOR 142, FOR 170; 250/339.12, 216, 225, 239, 334.04, 341.5, 435; 356/300, 303, 326, 327, 369, 36–38, 445; 345/428, 429, 430, 431, 432, 440, 507; 422/87.05–82.04, 68.1, 62, 105, 108, 119; 700/266

(56) References Cited

U.S. PATENT DOCUMENTS

| | | | | |
|---|---|---|---|---|
| 5,327,225 A | * | 7/1994 | Bender et al. | 356/445 |
| 5,468,968 A | * | 11/1995 | Bailey et al. | 250/435 |
| 5,808,903 A | * | 9/1998 | Schiltz et al. | 364/508 |

* cited by examiner

*Primary Examiner*—Hal Wachsman
(74) *Attorney, Agent, or Firm*—Wade James Brady, III; Frederick J. Telecky, Jr.

(57) ABSTRACT

A sensor control and data analysis system (100) for detecting and analyzing various (bio)chemical properties of a given sample substance (107) using an integrated SPR sensor (50) or other miniaturized sensor configuration. In one embodiment, raw sensor data from the sensing device (105) is transferred to a remote processing system (111), such as a desktop computer, having a display (125), keyboard or other user control and data entry device (123), internal storage area (127), internal microprocessor (117) and a communications means (129). The processing system (111) runs a software application program (115) that receives the raw sample data and perform qualitative and quantitative analysis to render meaningful information about the sample substance.

19 Claims, 13 Drawing Sheets

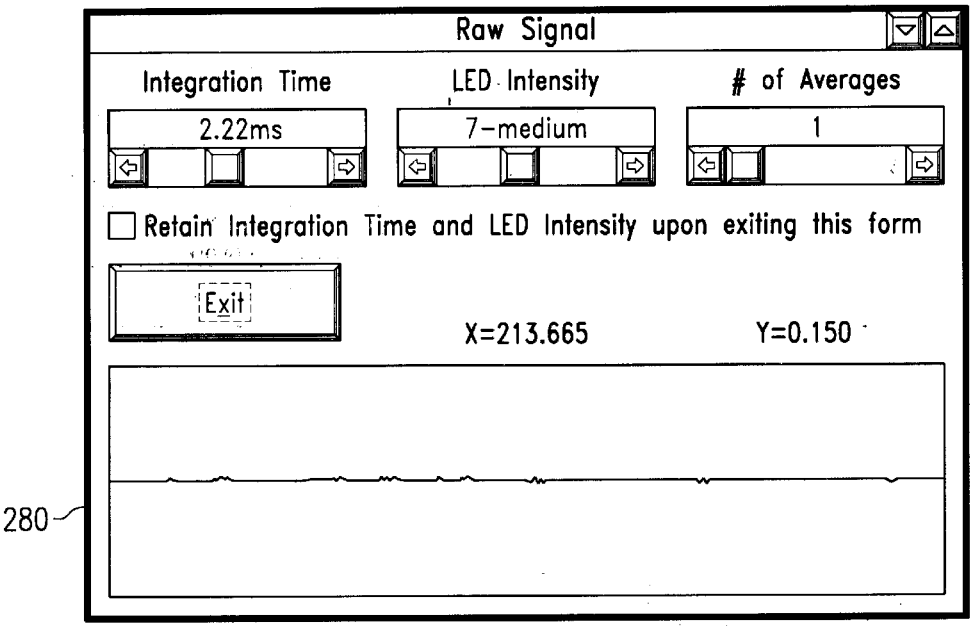
FIG. 17
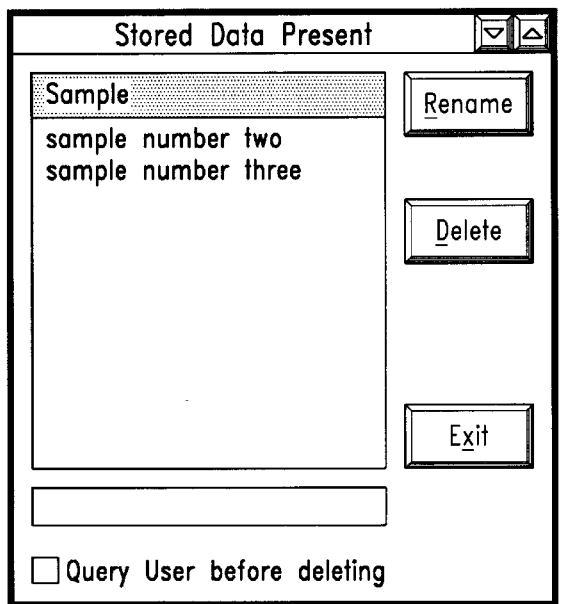
FIG. 18
| Pixel | Angle | Signal | Fit |
|---|---|---|---|
| 1 | 76.426 | .9568 | |
| 2 | 76.359 | .9575 | |
| 3 | 76.293 | .9561 | |
| 4 | 76.226 | .9535 | |
| 5 | 76.160 | .9505 | |
| 6 | 76.093 | .9568 | |
| 7 | 76.027 | .9534 | |
| 8 | 75.961 | .9546 | |
| 9 | 75.894 | .9527 | |
| 10 | 75.828 | .9483 | |
| 11 | 75.762 | .9465 | |
| 12 | 75.696 | .9454 | |
| 13 | 75.630 | .9530 | |
| 14 | 75.564 | .9489 | |
| 15 | 75.498 | .9444 | |
| 16 | 75.432 | .9470 | |
| 17 | 75.366 | .9561 | |
| 18 | 75.300 | .9530 | |
| 19 | 75.234 | .9492 | |
| 20 | 75.169 | .9459 | |
| 21 | 75.103 | .9402 | |
FIG. 19

FIXED OPTIC SENSOR SYSTEM AND DISTRIBUTED SENSOR NETWORK

CROSS REFERENCE TO PRIOR APPLICATIONS

This application claims priority under 35 U.S.C. 119(e) based upon provisional application Serial No. 60/029,976.

TECHNICAL FIELD

The present invention relates in general to the field of miniaturized optic sensors and more specifically to a software-based method and application for controlling sensor functions and analyzing sensor obtained data via an integrated graphical user interface.

BACKGROUND OF THE INVENTION

Without limiting the scope of the invention, its background is described in connection with an integrated miniaturized sensor combining a plurality of light optics and electronic components on a single platform for use in a wide array of (bio)chemical sensing applications.

Optic-based sensor systems have been developed and used in the fields of chemical, biological or biomedical analysis, process control, pollution detection and control as well as others. A typical application involves the chemical coating of a thin film, cable or other article followed by excitation and measurement in the presence of a given sample of interest. Various sensor configurations have been developed including Surface Plasmon Resonance ("SPR"), light transmission and fluorescence-based.

An integrally formed version of an SPR sensor includes a light source and detector array coupled to a light absorbing platform which is itself disposed inside a light transmissive housing. The housing is made of a material which is transparent to the radiation produced by the light source. The light source produces radiation that passes through the housing and strikes an exterior surface of the housing on which a thin layer of SPR material has been deposited. The light reflected from the conducting layer is directed toward the detector which comprises a linear array of n×1 photocells. The detector cell having the minimum output level is associated with radiation rays from the source that have bounced off the thin conducting layer at the "resonance" angle which is a function of the refracted index of the material contacting the SPR layer.

Recent advances in miniaturized low powered light sources and detectors have allowed the design of other sensor platform configurations including critical angle, chemiluminescence, colorimetric, visible and infrared spectroscopy, absorption, phase, photometry and others. A main feature of these miniaturized sensors is the fixed positioning of the light source, sampling surface and detector elements within a rigid solid housing.

While sensor configurations have been developed and used, methods for controlling sensor functions and operation have not been standardized. Routines and data analysis tools for characterizing, reproducing, storing and manipulating the sample data produced by such sensors are not currently available.

What is needed is a sensor control and data,analysis system that runs on a stand alone system, such as a desktop computer or workstation, and is operably linked to one or more sensor(s) which are in contact with the sample substance of interest. A sensor control and analysis application program which provides the user with a plurality of data and file functions via an on-screen interface would fill a much needed niche.

SUMMARY OF THE INVENTION

There are no readily available tools to control the function and operation of the miniaturized integrated sensor. A method and system of analyzing, manipulating and storing sensor obtained data is needed to facilitate the use of such sensors.

As such, it is a primary object of the present invention to provide a method and program for operating an SPR-based sensor and analyzing the data for use in a wide array of miniaturized sensor applications.

Another object of the invention is to provide such a program that can be implemented and used in conjunction with other sensor platforms including but not limited to, critical angle sensors, light transmission sensors, fluorescence-based sensors and others.

Disclosed in one embodiment of the invention is a sensor control and data analysis system for detecting and analyzing various (bio)chemical properties of a given sample substance using a miniaturized integrated sensor. In one embodiment, raw sensor data from the sensor is transferred to a remote processing system, such as a desktop computer, having a display, keyboard, or other user control and data entry device, internal storage area, internal microprocessor and a wireless communications subsystem. The processing system runs a software application program that receives the raw sample data and performs qualitative and quantitative analysis to render meaningful information about the sample substance. The application program includes a plurality of information screen areas in the form of a graphical user interface having at least an analysis region, a plot region, a sensor setting region and a sensor status region among others.

BRIEF DESCRIPTION OF THE DRAWINGS

In the drawings:

FIG. 17 illustrates a screen shot of a view raw signal screen according to one embodiment of the sensor control system of the present invention;

FIG. 18 illustrates a screen shot of a stored data screen according to one embodiment of the sensor control system of the present invention;

FIG. 19 illustrates a table of displayed data listing angle and signal information versus pixel number according to one embodiment of the sensor control system of the present invention.

Corresponding numerals and symbols in the different figures refer to corresponding parts unless otherwise indicated.

DETAILED DESCRIPTION OF THE PREFERRED EMBODIMENT

Figure 1:
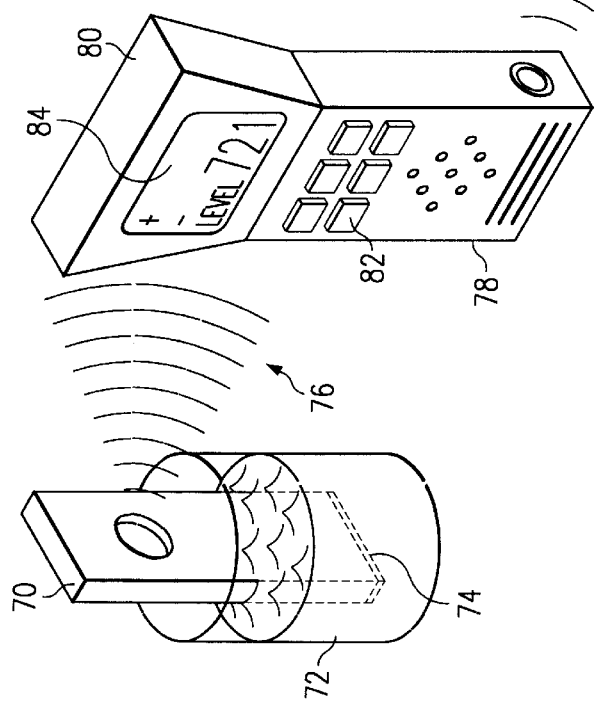
FIG. 1 is a side profile view of a miniaturized integrated formed Surface Plasma Resonance ("SPR") sensor.
Figure 1:
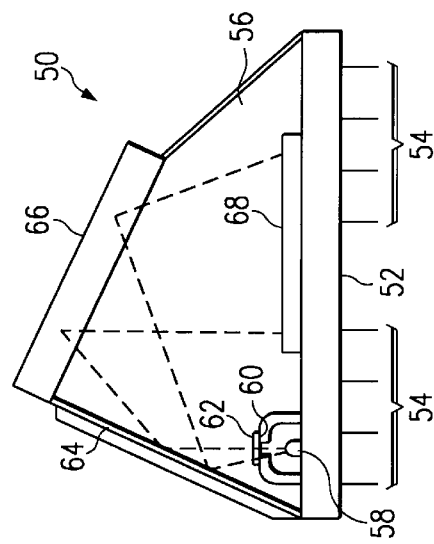

In FIG. 1 an integrally formed Surface Plasmon Resonance ("SPR") sensor 50 is shown. A substrate 52 forms a device platform to which a light transmissive housing 56 is coupled. A light source 58 is preferably located above or within the substrate 52 and has an aperture 60 thereover allowing light to pass. A polarizer 62 is located near the aperture 58 to polarize passing light which, in turn, continues through housing 56 and strikes a SPR layer 64 which is preferably formed on an exterior surface of the housing 56. The SPR layer 64 may be deposited or placed on a glass slide or the like. This configuration achieves an optical surface phenomenon that can be observed when the polarized light is totally internally reflected from the interface between the layer 64 and the sample of interest (not shown in FIG. 1).

As shown, a mirrored surface 66 directs the reflected light onto a detector array 68 which senses illumination intensity of the reflected light rays. For optical radiation, a suitable photodetector 68 is the TSL213, TSL401, and TSL1401, with a linear array of resolution n×1 consisting of n discrete photo sensing areas, or pixels. Light energy striking a pixel generates electron-hole pairs in the region under the pixel. The field generated by the bias on the pixel causes the electrons to collect in the element while the holes are swept into the substrate. Each sensing area in the photodetector 68 thereby produces a signal on an output with a voltage that is proportional to the intensity of the radiation striking the photodetector 68. This intensity and its corresponding voltage are at their maxima in the total internal reflection region. A lead frame 54 is coupled to one end of the substrate 52 and provides a signal pathway from the detector 68 output to the external world.

FIG. 1 depicts an SPR sensor 50 which can be used in conjunction with the sensor control and analysis system of the present invention. It should be understood, however, that other miniaturized sensor configurations may also be used including critical angle, light transmission and fluorescence-based sensor platforms. Other suitable configurations will be apparent to those skilled in the art upon reference to this disclosure and it is intended that such uses be covered by the invention.

Figure 2:
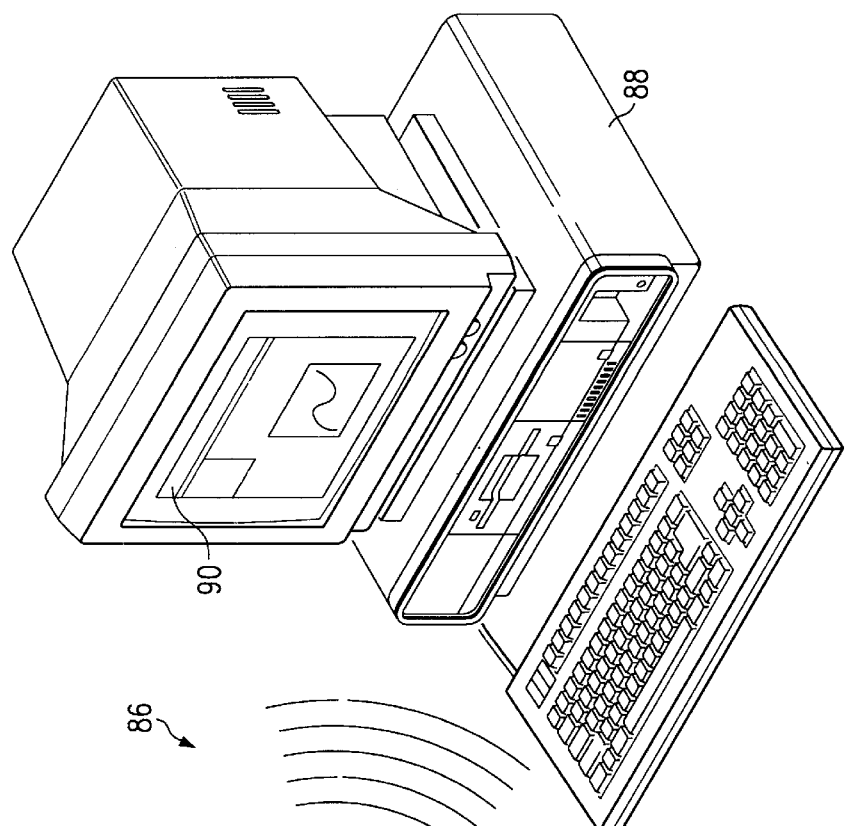
FIG. 2 illustrates use of a miniaturized integrated sensor device in a practical field application.

Turning now to FIG. 2, a practical application of a miniaturized integrated sensor 70 is shown wherein the sensor 70 has been immersed in a liquid sample 72, causing the sample 72 to make contact with a sensor 70 along sensor/sample surface 74. As is appreciated by those skilled in the art, the liquid sample 72 causes a change of light reflected off the sensor/sample surface 74 due to differences in refractive index. This change is detected by the sensor 70 via an internal detector (not shown) and communicated 76 to instrument 78. In one of the preferred embodiments, a wireless communications-system is used to transfer the raw sensor data from the sensor 70 to the instrument 78. Also, the instrument 78 can control sensors via the wireless communications system.

The instrument 78 consists of an instrument enclosure 80 having user controls 82 and display 84 which renders visual information about the sample 72 to the user. The sample related data can be stored, processed, analyzed or otherwise manipulated. Also, the sample data may be transmitted 86 to a remote processing system 88 which has sensor control and analysis software 90 executing thereon. As shown, the interface between the instrument 78 and remote processing system 88 may also be wireless although it should be understood that a physical interface may also be used.

The remote processing system 88 executes a sensor control and data analysis application program 90 which is the subject of the present invention.

Figure 3:
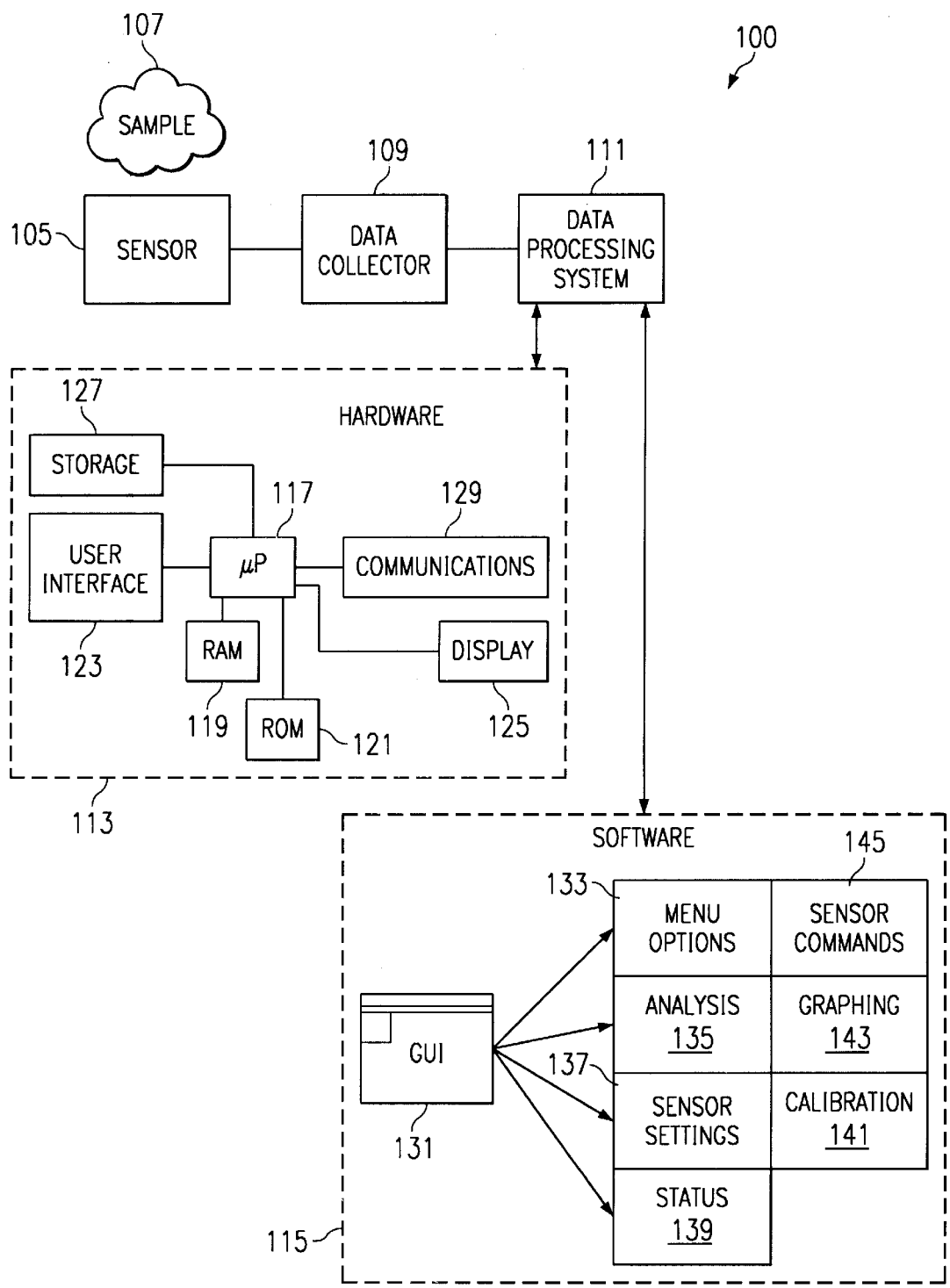
FIG. 3 is a block diagram of a complete sensor control system according to one embodiment of the invention.

In FIG. 3, a sensor control and sample analysis system according to the invention is shown and denoted generally as 100. System 100 includes a miniaturized sensor 105 that is placed near or in contact with a particular sample of interest 107 to permit detection of various biochemical properties of the sample 107. The sensor 105 may be an SPR-based sensor 50 or other miniaturized sensor platform such as fluorescence-based, critical angle and light transmission configurations all of which are suitable sensor 210 types. Other sensor platforms include chemiluminescence, colorimetric, visible and infrared spectroscopy, absorption, phase, photometry and others (bio)chemical sensing methods, all of which are known by those skilled in the art.

A data collector 109 is communicably linked to the sensor 105 via wireless or physical link and arranged to receive the output signals of the detector device inside the sensor 105. In one embodiment the data collector 109 is a portable hand held instrument which field personnel take with them to the sample location. In another embodiment the sensor 105 and data collector 109 are combined into a single sensing device which collects, gathers and stores the sample related data in a single instrument.

As shown, a data processing system 111 is communicably coupled to the data collector 109 via wireless or physical link. The data processing system 111 may be a desk top computer, work station or dedicated processor which contains a plurality of software routines and algorithms which analyze the data obtained by the data collector 109. As shown, the data processing system 111 consists of a hardware subsystem 113 and a software subsystem 115.

Turning first to the hardware subsystem 113, a microprocessor 117 is provided which performs the various algorithmic and system control functions of the system 100. The hardware subsystem 113 has memory area 119 which may be static or dynamic Random Access Memory and is used by the micro-processor 117 during operation. Likewise, a Read Only Memory area 121 is provided to store permanent system routines used by microprocessor 117.

The hardware subsystem 113 has a user interface 123 such as a keyboard, mouse or other user controlled means of entering data and operating the hardware subsystem 113. Display 125 may be a video terminal, CRT, liquid crystal display or other similar display means used to render visual information to the user regarding the sample, data analysis and other system function settings and or commands. The analysis results and other system variables can be stored in storage area 127, such as a hard disk, floppy drive, flash memory, tape back up or other similar means of storage. Also shown is a communications device 129 which is used to link the hardware subsystem 113 to the outside world.

The software subsystem 115 has a Graphical User Interface ("GUI") 131 to the various system functions, routines, commands and other features which allow user control and operation of the sensor 105 and platform analysis of the sample related data obtained by the sensor 105 and collected by the data collector 109. The GUI 131 comprises a screen display with various regions including, but not limited to, analysis region 135, settings region 137, sensor status region 139, calibration region 141, graph region 143 and sensor commands region 145.

The various regions 133, 135, 137, 139, 141, 143, and 145 of GUI 131 are part of a sensor control and analysis application program which the user accesses via GUI 131 to operate the sensor 105 and analyze the sample related data obtained by sensor 105 and collector 109. A menu bar 133 allows the user to select from a plurality of system, file and data analysis options as herein described.

Figure 4:
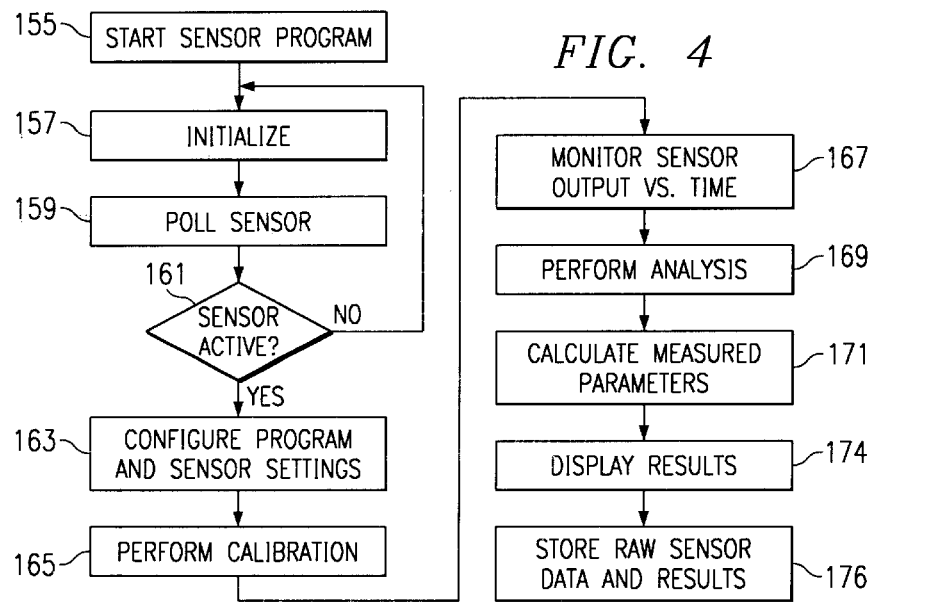
FIG. 4 is process flow diagram illustrating their method of use for the sensor control program of the present invention.

Turning now to FIG. 4, a process flow diagram 150 is shown detailing the method of use and operation for the sensor control and operation program of the present invention. Process 150 starts wherein the user initiates the sensor program step 155, by activating the data processing system 111 and executing the software subsystem 115. Next, the software program runs an internal initialization routine, step 157, such as a power-on-self-test or initial system check and diagnosis to insure the various system components are active and functioning. The sensor 105 is polled to insure that light source and detector components are responding and ready to take sample measurements. If the sensor is not detected at step 161, system flow is directed toward block step 157 until sensor activity is detected.

In step 163, after the sensor 105 is detected, the program and sensor are configured according to user selected settings which may be stored in an initialization file and loaded at power up. The user can configure the intensity of the light source within the sensor 105 and determine the integration time period used to accumulate the sensor data. Other options are also made available to the user as is described herein.

Next, process flow is directed to step 165 wherein the sensor 105 is calibrated in order to compensate for any imperfections, formations or other aspects of the sensor/sample interface. For SPR calibration, step 165 involves three sensor measurements. These measurements can be illustrated with reference to FIG. 3, where the sensor takes an air reference measurement after the user pulls the sensor 105 away from the sample 107. The air reference is used to compensate for any surface imperfections that exist along the sensor/sample interface. The sensor 105 is then placed in contact with the sample 107 and a background reference is established by taking a set of data. The background reference takes into account light impacting the sensor that is not originating from the sensor light source. A correction factor is then determined using the following expression for a given sample measurement:

$$\frac{Sample - Background}{Air - Background}.$$

Extended Area Calibration

In one embodiment, the calibration step 165 uses multi-point, or extended area, interaction to embed additional information in the sensor resonance curve for increasing measurement confidence, or fault detection. This approach is critical for practical use of SPR sensing in an uncontrolled, field environment.

Prior art calibration methods utilize a focused beam, single point SPR excitation which is "blind" to nonuniform adlayers resulting from non-specific adsorption of macroscopic interferants, as one might expect to find in a muddy, or sludge-like, sample without sensor rinsing. The response to such a bounce surface is a standard resonance curve with a minimum reflectance at an angle indicative of an average of the adlayer effect. This represents an erroneous result, or false alarm!

The extended area approach includes features, or "bumps" in the SPR spectrum indicating the adsorption of interference to the surface, and is indicative of a problem, or fault. The lack of macroscopic non-uniformities results in the observation of a standard resonance curve which, in the extended area approach, implies a reliable measurement has been obtained by SPR.

Figure 20:
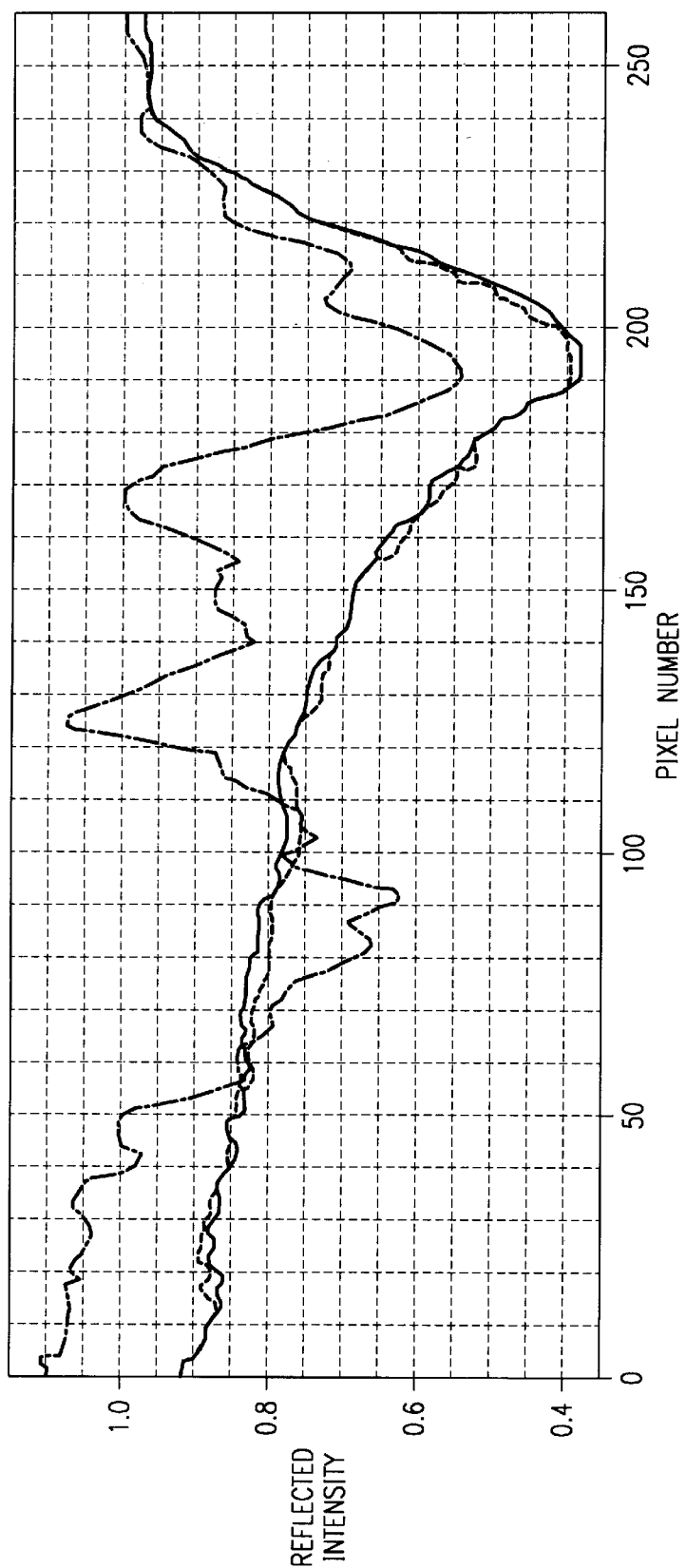
FIG. 20 is a graph of resonance curves demonstrating advantages of extended area calibration.

The advantages of the extended area approach are further appreciated by reviewing the experimental results obtained using the extended area calibration to measure the refractive index of water, powder in water, and water-based sludge. The resulting resonance curves are shown in FIG. 20 wherein the resonance curve for the powder solution and water are nearly identical, indicating that adsorption of powder to the surface is minimal. However, the exposure of the surface to sludge, with high macroscopic particulate content, does result in surface contamination, or fouling, when no subsequent rinsing step is employed. This is indicated in the substantially featured "resonance curve" observed in the sludge, and shown in FIG. 20. The lack of tight binding between the sludge and the sensor was confirmed when a simple water rinse resulted in a clean surface, and recovery of the original SPR curve in water. A single-point measurement would have simply, and erroneously, indicated a different refractive index for the sludge, without recognizing that the surface had been fouled.

After calibration 165, the sensor 105 is ready to take sample measurements and the program monitors the sensor detector output versus time, step 167, to obtain a plurality of time driven sample measurements. The data is transferred to processing system 111 where it is analyzed 169 to obtain meaningful information about the sample of interest 107. As is appreciated by those skilled in the art, in step 171, numerous qualitative and quantitative factors may be determined from the sample data including the sample index, the broadness of the refractive index curve over time and the intensity of the light as a function of pixel number.

Next, in step 174, the results are displayed as a table of raw data points, a graph or plot of the data points versus time, a minimum and maximum point over the sample period or other similar display method. The user is given the option of storing the raw data and analytical results 176 on a magnetic storage means such as a hard disk or floppy drive or a hard copy output may be printed. Other options are also available to the user as explained herein and as understood by those skilled in the art.

Figure 5:
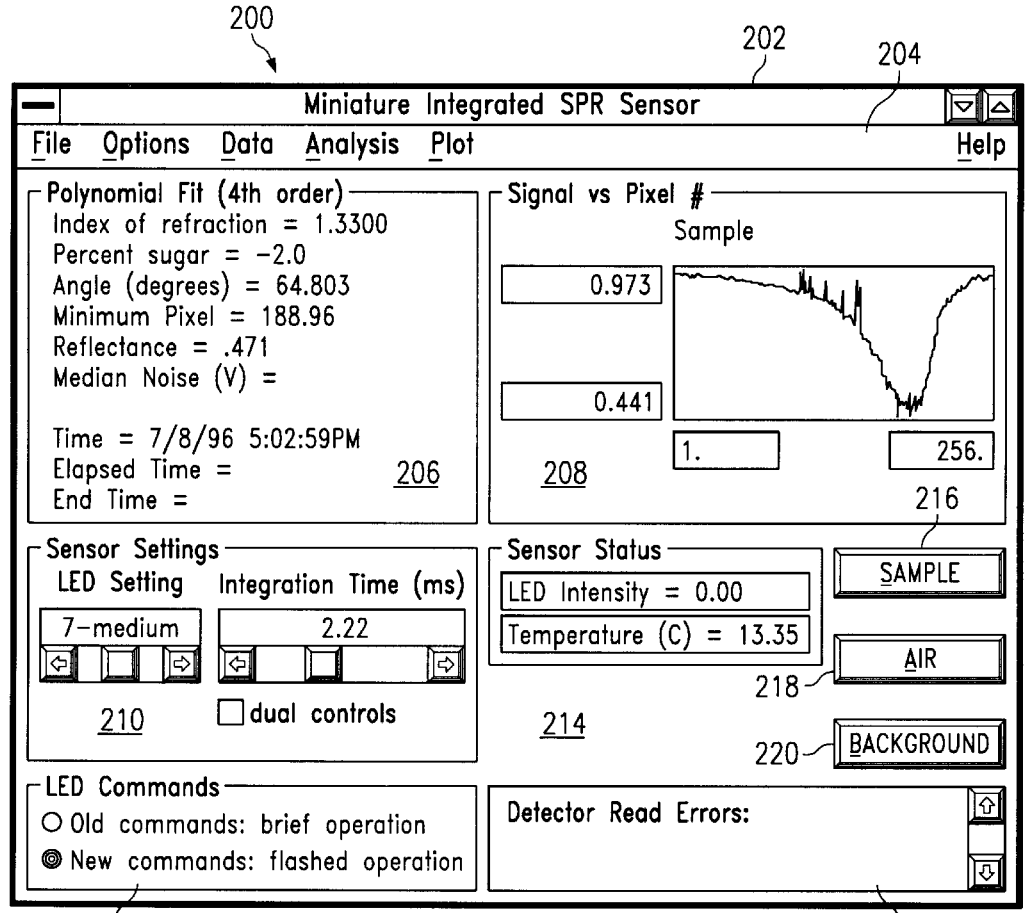
FIG. 5 is a Graphical User Interface ("GUI") for an integrated sensor control and data analysis program according to one embodiment of the invention.

Turning now to FIG. 5, a GUI of a sensor control and operation program 200 according to one contemplated embodiment of the invention is shown. The GUI 200 has a border 202 surrounding a plurality of screen regions which provide analytical information about the sample and give the user control over various sensor functions. A menu bar 204 is provided which gives the user access to other options and screens within the program and allows the user to alter program characteristics.

At the upper left hand corner of the GUI 200 an analysis region 206 is found which displays analysis results for the sensor data. For example, with a compound containing sugar, the analysis region 206 can display the index of refraction for the compound, the percent sugar in the compound, the angle at which minimum light intensity was detected, the pixel number where the minimum light is detected, reflectance value at that point and the medium value of noise at that point. The date and time of which sensor data was taken and total elapsed time during the sampling period are also provided in region 206.

A plot region 208 is shown at the upper right hand corner of the GUI 200 which renders a graphical representation of the light signal amplitude versus the pixel number of the detector. Various methods of altering the display 208 are provided wherein the user can change the Y and the X axis scales, zoom in on a particular area or display numerical values at a given data point. Other options are available to the user as is appreciated by those skilled in the art.

At the lower left hand portion of the GUI 200 is a sensor settings region 210 wherein the user can select the LED intensity setting the lights corresponding to the intensity of the light source of the sensor and the integration time to determine the length of time used to accumulate the sensor data. Below region 210 is a light source command section 212 wherein the user can activate or deactivate the light source. The lower right hand portion of the GUI 200 has a sensor status region 214 wherein current sensor settings are displayed to show the intensity of the light source and the temperature of the sensor.

A sample button 216, reference button 218 and background button 220 which allow the user to compensate for surface imperfections along the sensor/sample interface. The reference button 218 causes the sensor control program to establish a reference point for signal measurements and provides a way of correcting for spatial intensity variations. The background button 220 is used to adjust for light that hits the detector not originating from the self-contained LED. An error region 222 notifies the user of any system wide errors which may occur during the operation of the sensor or analysis of the sensor data.

Figure 6:
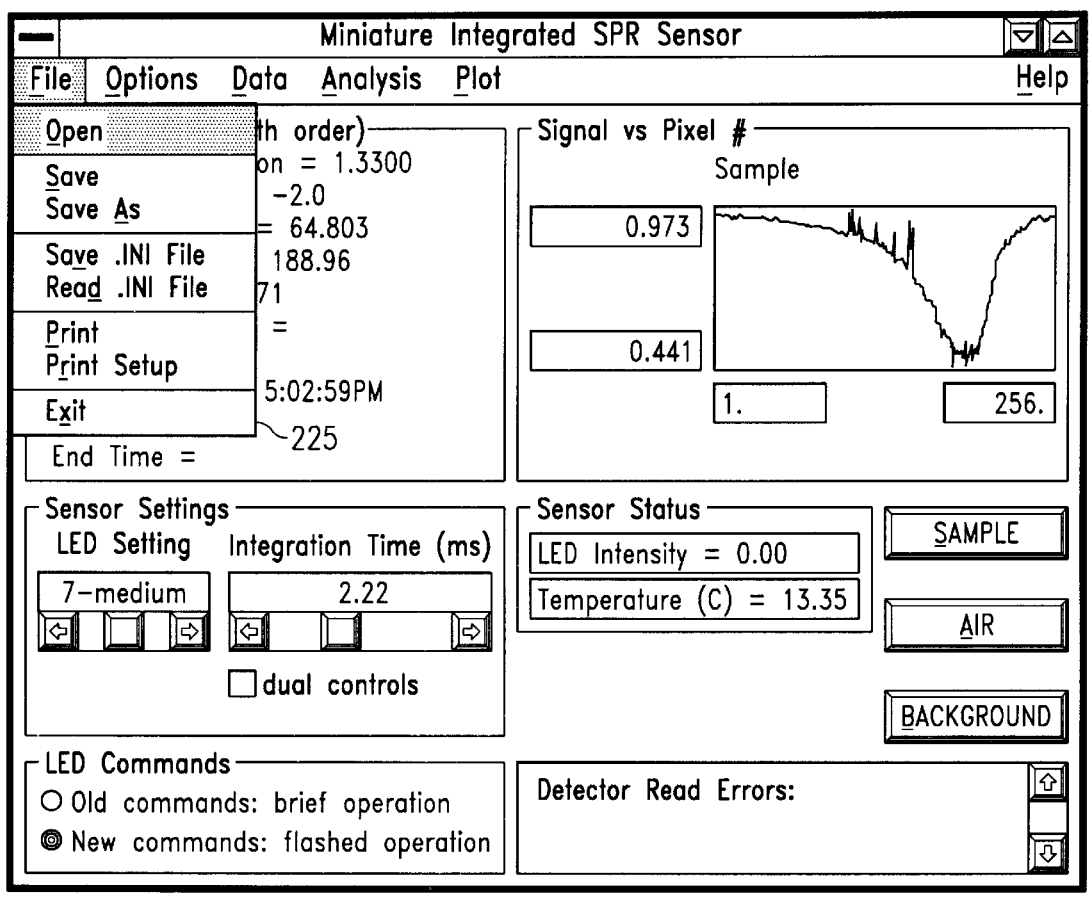
FIG. 6 illustrates the file menu options of the GUI illustrated in FIG. 5.

Turning now to FIG. 6, the file menu options of the GUI 200 are illustrated and denoted generally as 225. As illustrated in the file options 225, the user has the option of opening a previously stored data file, saving a data file, saving a data file with a particular name, saving the initialization file to restore program parameters upon initialization reading a initialization file, printing the main contents of the graphical user interface at a give time, altering the printer settings or exiting the program.

Figure 7:
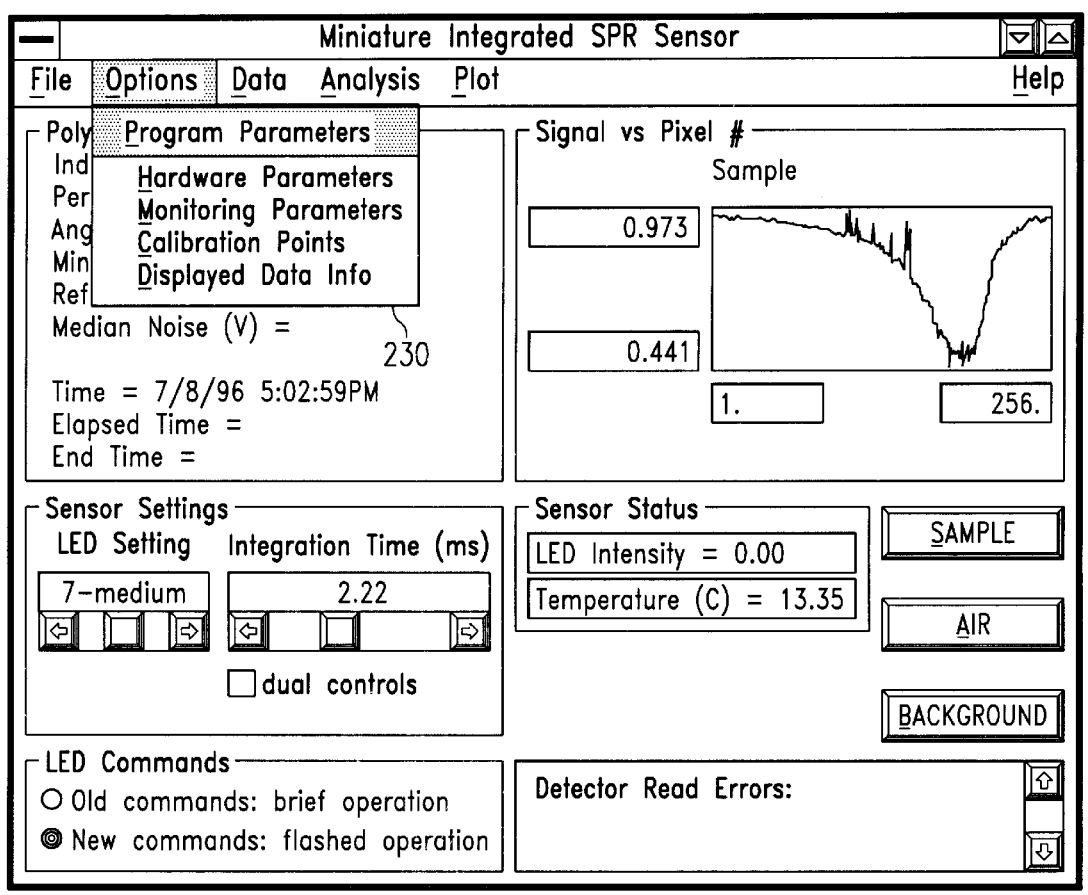
FIG. 7 illustrates the option menu options of the GUI illustrated in FIG. 5.
Figure 8:
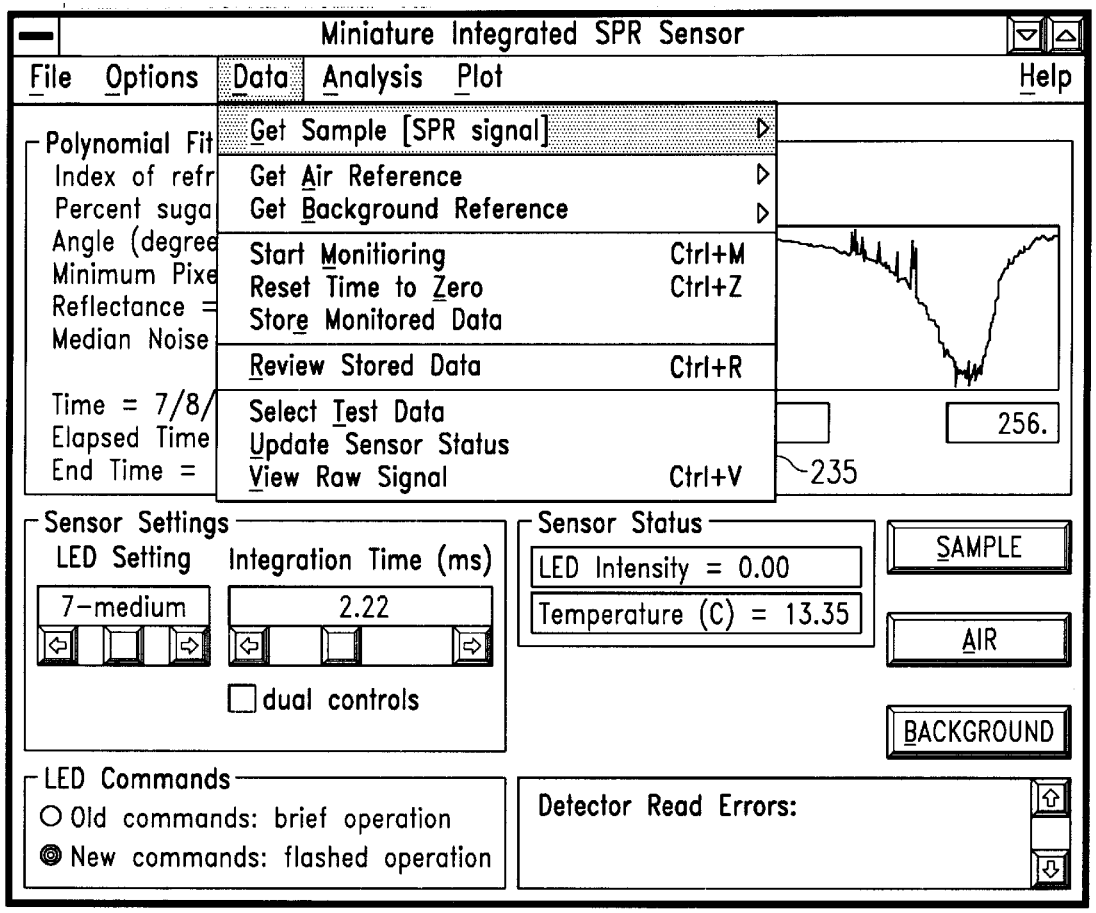
FIG. 8 illustrates the data menu options of the GUI of FIG. 5.

In FIG. 7, the option menu items of the GUI 200 are illustrated by pull down menu 230. The various options under menu 230 allow the user to activate other graphical user interfaces to various program and sensor settings as well as other system options. In particular, the user has access to program parameters, hardware perimeters, monitoring perimeters, calibration points and displayed data information. In FIG. 8, the data menu items are illustrated n pull down menu 235 giving the user various selections including get sample, get reference, get background references, start monitoring, reset time to zero, store monitor data, review store data, update sensor status and view raw signal data among others.

Figure 9:
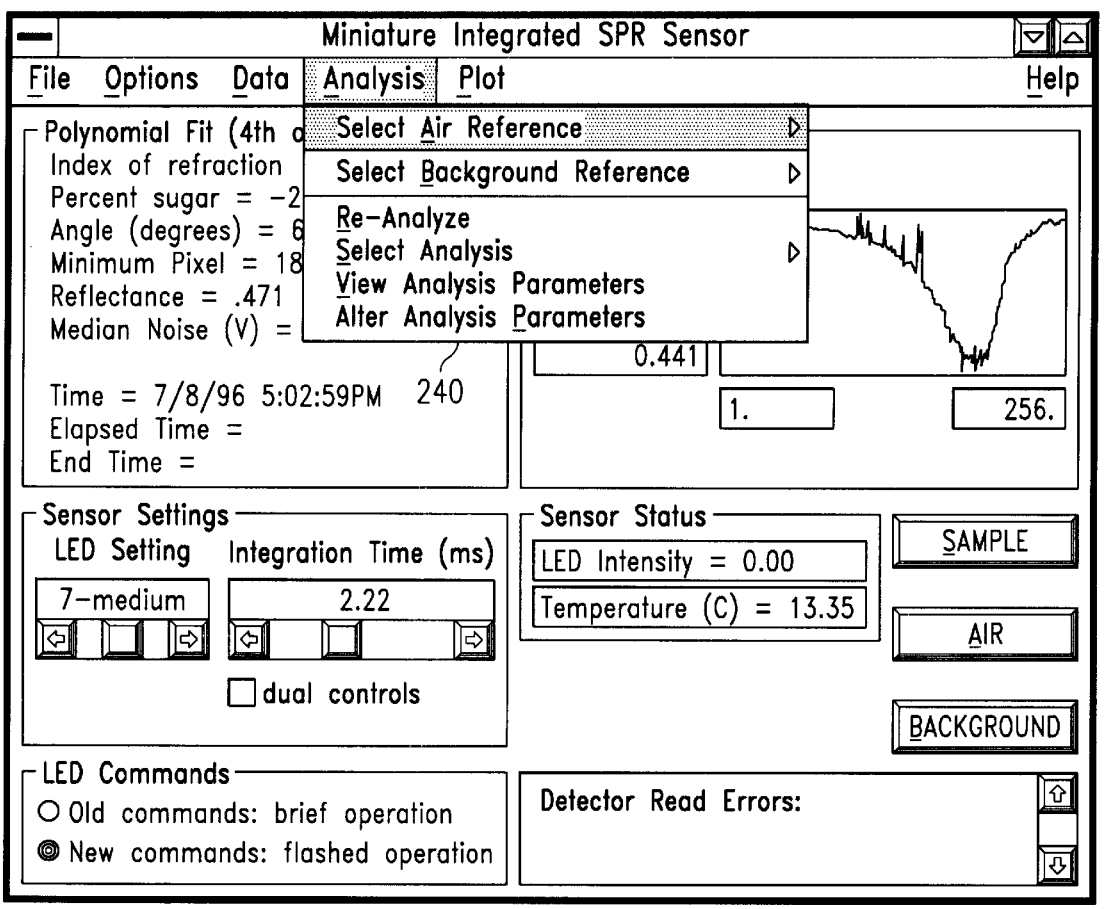
FIG. 9 illustrates the analysis menu options of the GUI of FIG. 5.

Turning now to FIG. 9, the analysis options are shown in pull down menu 240 providing various data analysis options to the user. The user can select the reference, select the background reference, reanalyze, select analysis, view analysis parameters and alter analysis parameters.

In one contemplated embodiment, several different analysis types are contemplated to achieve algorithmic fits of the sample data. Examples include a polynomial fit about the approximate minimum value, a determination where the derivative of the signal curve goes to zero, and a determination of the minimum value of the data along the signal curve, and determination of the first moment. Other methods of analysis may also be provided all within the scope of the present invention.

Figure 10:
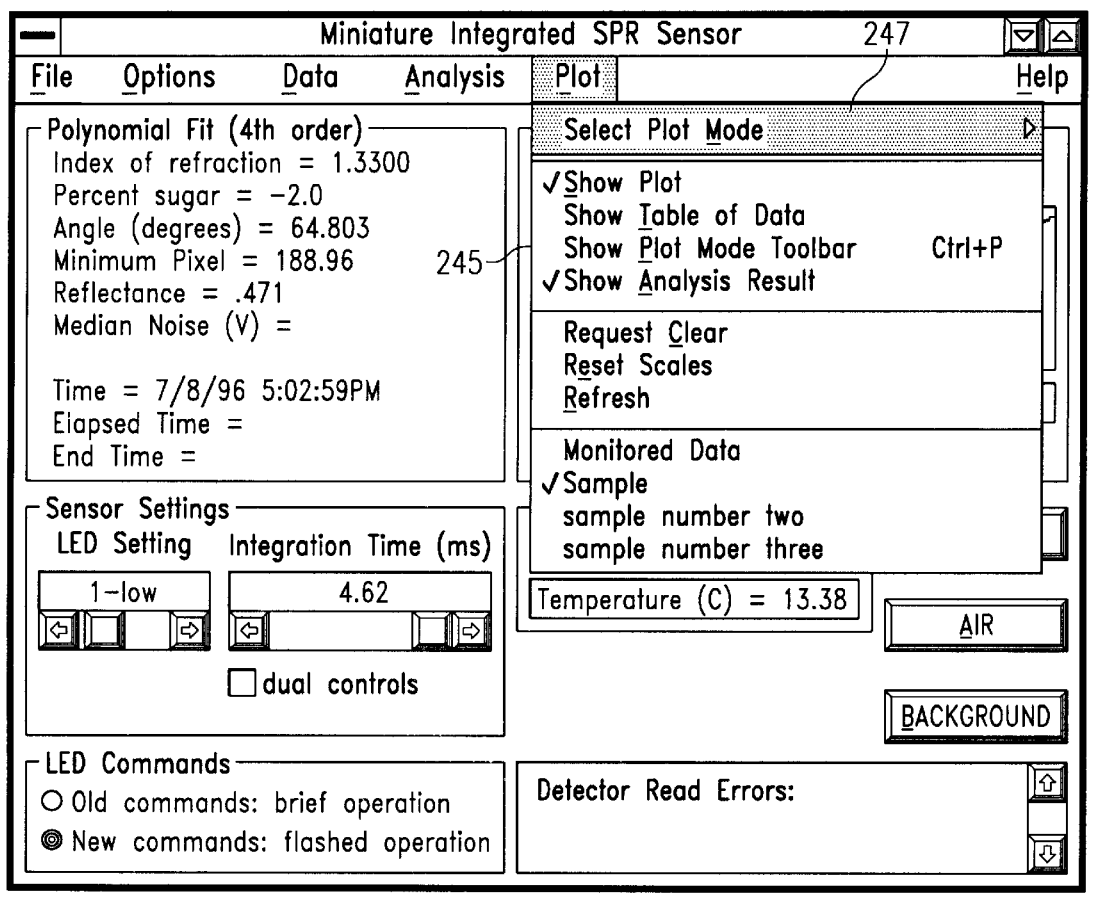
FIG. 10 illustrates the plot menu options of the GUI of FIG. 5.

Turning now to FIG. 10, pull down menu 245 illustrates the plot menu option the user various ways of displaying the sample data as well as the real time monitor data. As shown, menu 245 gives the user the option to select a plot mode corresponding to the X and Y-axis of the data graph in plot region 208. The user may show the plot or make the plot visible or invisible. The user may also activate a data table representation of the sample data, pull up a plot mode toolbar or show the analysis results in the corresponding plot region 208. Other options include request clear, reset scales and refresh. Also pull down menu 245 allows the user to check the corresponding stored signal to display in region 208.

Figure 11:
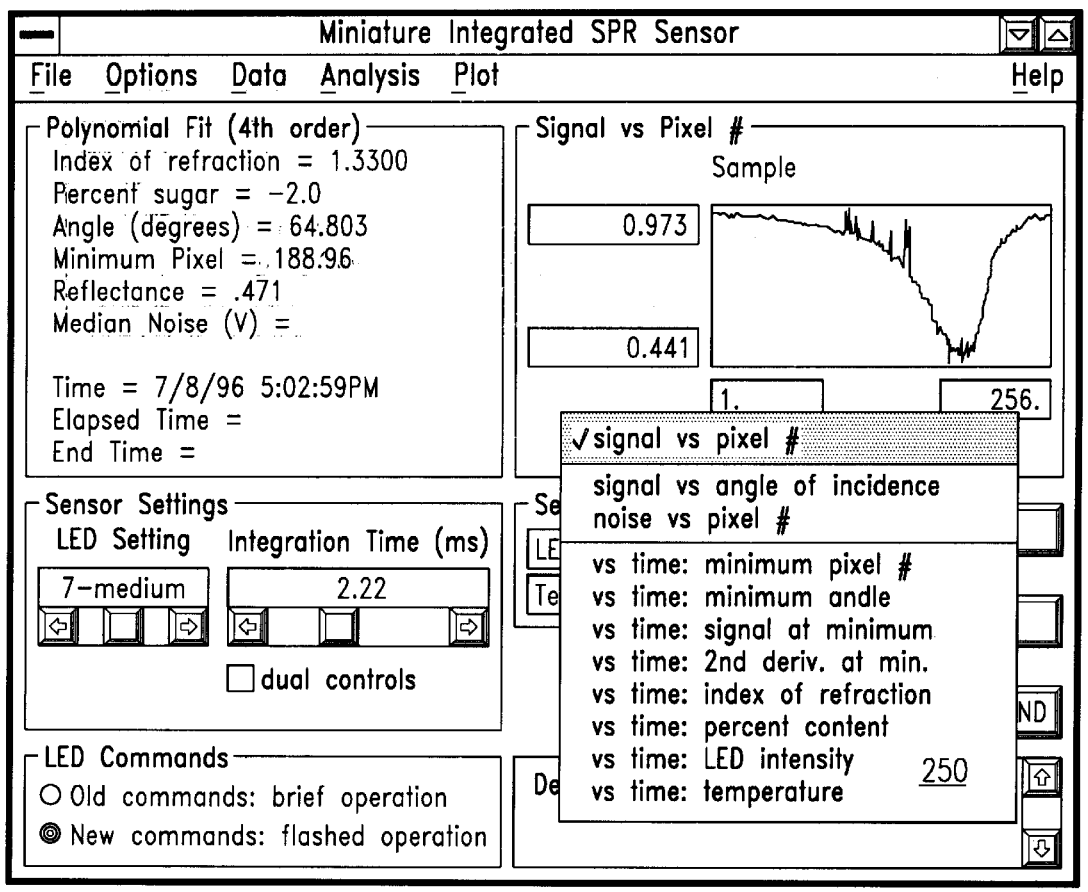
FIG. 11 illustrates various plot mode options according to one embodiment of the sensor control system of the present invention.

The plot made options available to the user when select plot mode is chosen from menu 245 are illustrated in FIG. 11 in menu 250. Menu 250 provides the user with 11 ways of displaying data, including signal versus pixel number, signal versus angle of incidence, noise versus pixel and others.

Figure 12:
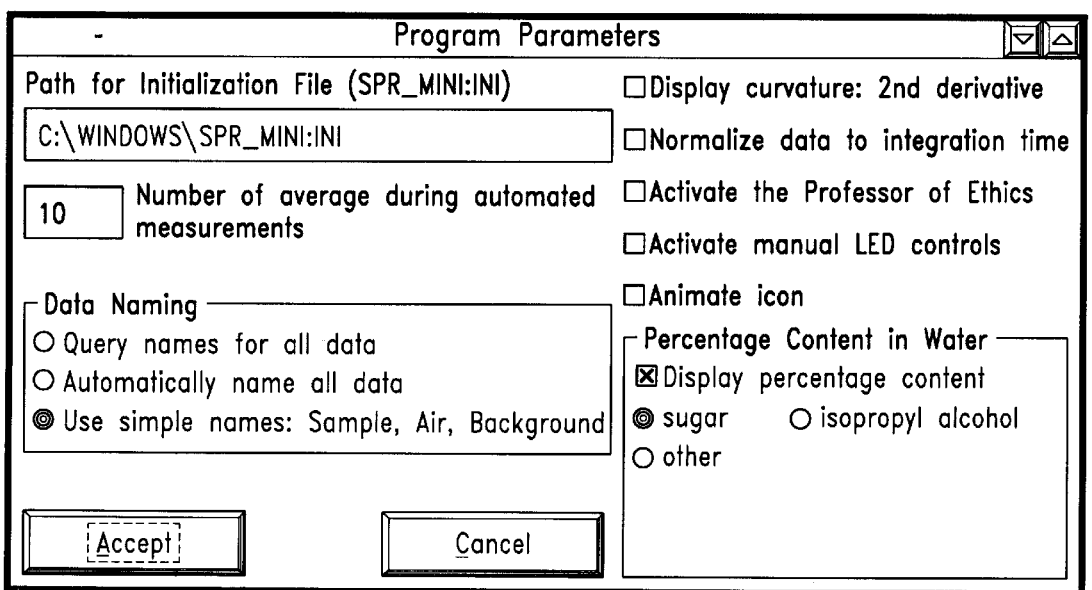
FIG. 12 illustrates various program parameters according to one embodiment of the sensor control system of the present invention.

FIG. 12 illustrates the program parameters GUI obtained through the program parameters option of pull down menu 230. The user can customize a plurality of program parameters which determines how the program analyzes the raw sensor data as well as other program features.

Figure 13:
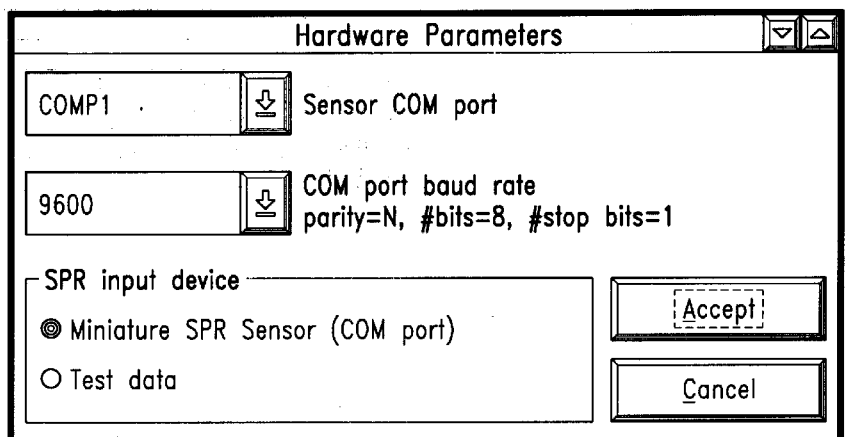
FIG. 13 illustrates various hardware perimeters according to one embodiment of the sensor control system of the present invention.

The hardware parameters are illustrated in FIG. 13 by GUI 260 which controls the various communication features of the data processing system 111 for communications with the data collector 109.

Figure 14:
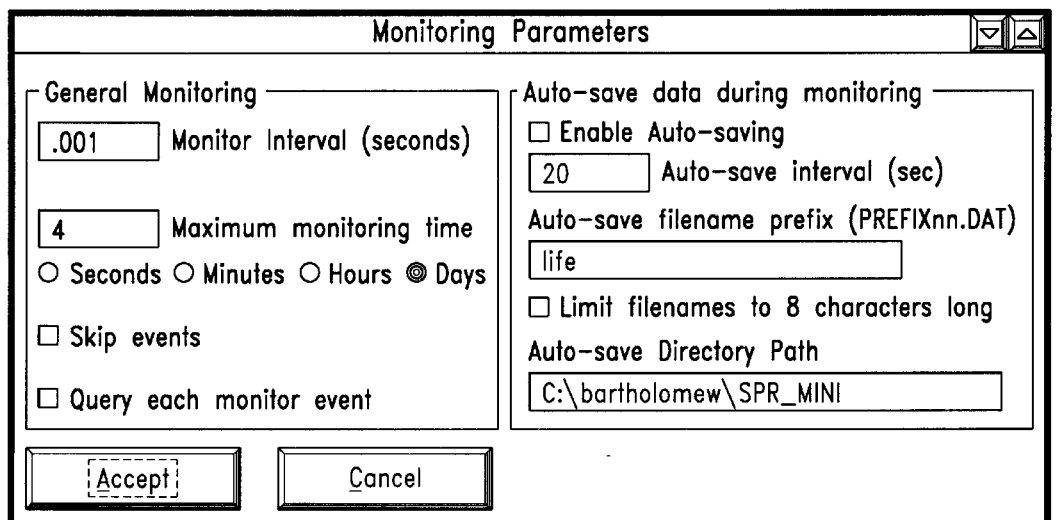
FIG. 14 illustrates the various monitoring perimeters according to one embodiment of the sensor control system of the present invention.

FIG. 14 shows the monitoring parameters via GUI 265 which allows the user to select and alter a plurality of sampling variables which determine the frequency and duration in which incoming sensor data is sampled.

Figure 15:
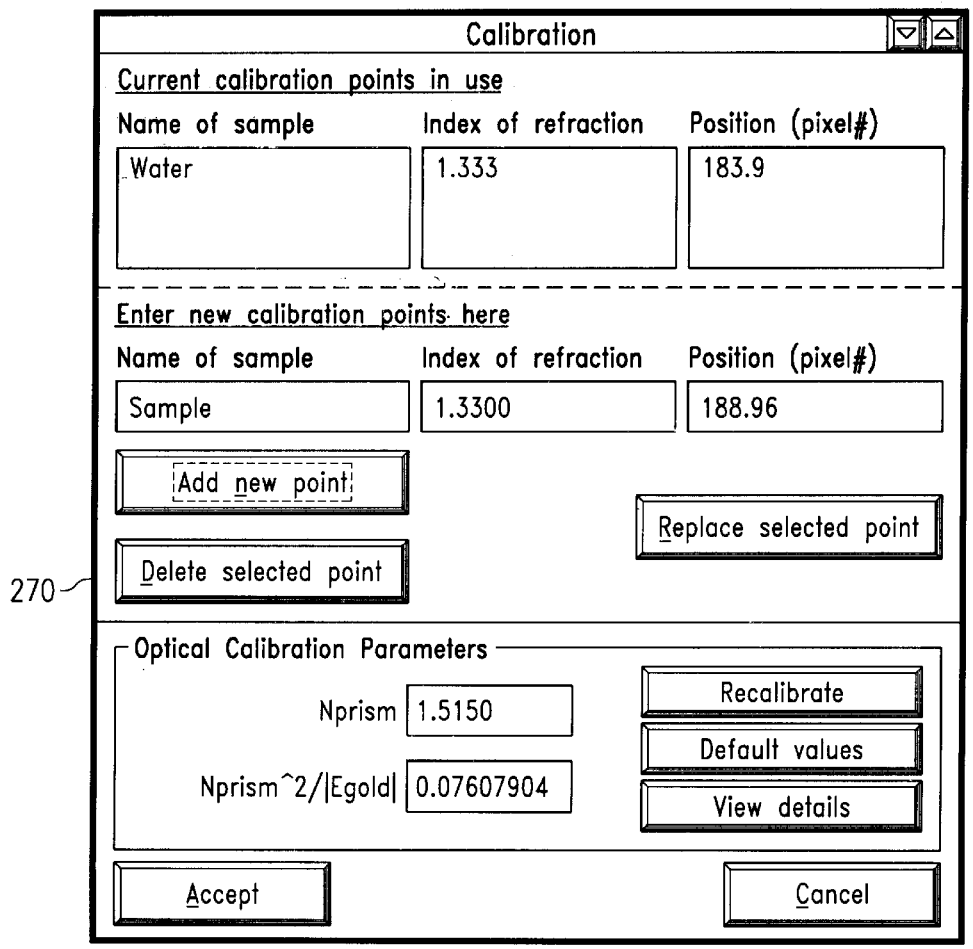
FIG. 15 illustrates various calibration settings according to one embodiment of the sensor control system of the present invention.

In FIG. 15, the calibration GUI 270 is shown which allows the user to add, delete or replace the calibration points in order to adjust the analysis for any debris or surface imperfections that exist on the sensor/sample interface.

Figure 16:
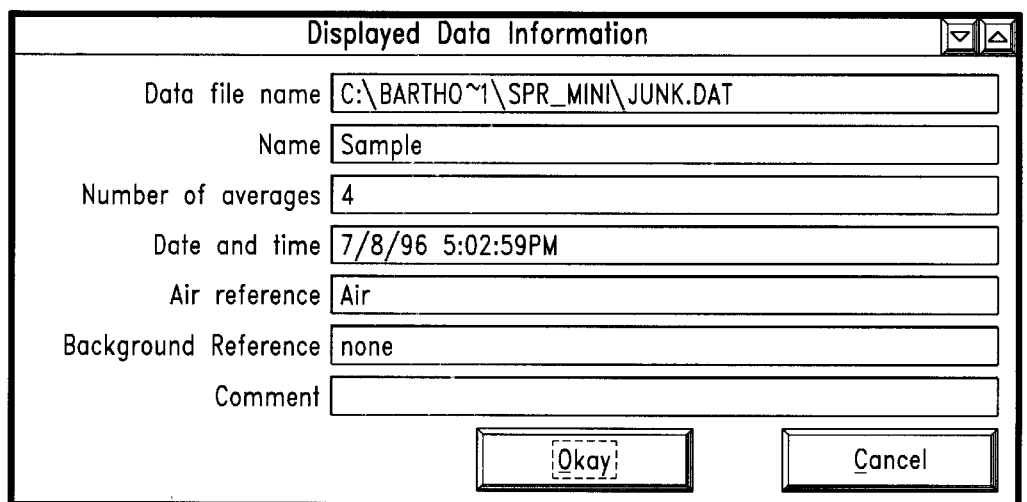
FIG. 16 illustrates a screen shot of a display data information screen according to one embodiment of the sensor control system of the present invention.

In FIG. 16, the display data information screen 275 is shown which provides the user with a quick summary of the current set of sample data.

In FIG. 17, the raw signal user interface 280 is illustrated providing the user a snapshot view of sample analysis settings including the integration time, the light source intensity and number of averages taken during a given sampling period.

FIG. 18 shows a stored data present screen 285 which lists for the user the current stored data files which are available on the system and allows the user to rename or delete the files.

FIG. 19 is a raw data table screen 290 which lists the angle and signal strength at each point per each pixel number of the sensor detector array.

What is claimed is:

1. A method of analyzing at least one of various chemical and biochemical properties of a given sample comprising the steps of:
   providing a sample to be analyzed;
   providing a sensor having a plural element detector array;
   providing a light source;
   turning ON the light source;
   determining whether said sensor is operating;
   responsive to a determination that the sensor is operating, placing said sensor remote and spaced from said sample to be analyzed;
   turning OFF the light source;
   taking a background reference sample measurement with said sensor to determine the intensity of reflected light impinging on said sensor not originating from the light source;
   with said light source ON, placing said sensor in sufficiently close proximity to said sample to be analyzed to provide a sensor/sample interface and to obtain a sample measurement of said sample to be analyzed;
   taking a sample measurement of said sample to be analyzed;
   obtaining air reference, background reference and sample reference measurements; and
   using said air reference, background reference and sample reference measurements to determine a correction factor and provide a corrected measurement of said sample to be analyzed.

2. The method of claim 1, wherein said steps of taking a sample measurement of said sample to be analyzed and using said air reference, background reference and sample reference measurements to determine a correction factor farther comprise the steps of:
   turning ON the light source;
   taking a plurality of said sample measurements to provide a signal amplitude corresponding to each sample measurement;
   reading the corresponding signal amplitude of light reflected from the sensor/sample interface;
   adjusting each analysis of said at least one of various chemical and biochemical properties of said given sample by said correction factor;
   storing the sample measurements in a sample file; and
   plotting the sample measurements as a function of time.

3. The method of claim 2 wherein said light source is a laser.

4. The method of claim 3 wherein the intensity of said light source is under control of said correction factor.

5. The method according to claim 4 further comprising the step of calibrating all sample measurements at said plural elements of said detector array.

6. The method according to claim 3 further comprising the step of calibrating all sample measurements at said plural elements of said detector array.

7. The method of claim 2 wherein the intensity of said light source is under control of said correction factor.

8. The method according to claim 7 further comprising the step of calibrating all sample measurements at said plural elements of said detector array.

9. The method according to claim 2 further comprising the step of calibrating all sample measurements at said plural elements of said detector array.

10. The method according to claim 1 further comprising the step of calibrating all sample measurements at said plural elements of said detector array.

11. The method of claim 10 wherein the intensity of said light source is under control of said correction factor.

12. The method according to claim 11 further comprising the step of calibrating all sample measurements at said plural elements of said detector array.

13. The method according to claim 20 further comprising the step of calibrating all sample measurements at said plural elements of said detector array.

14. The method of claim 1 wherein said light source is a laser.

15. The method of claim 14 wherein the intensity of said light source is under control of said correction factor.

16. The method according to claim 15 further comprising the step of calibrating all sample measurements at said plural elements of said detector array.

17. The method according to claim 14 further comprising the step of calibrating all sample measurements at said plural elements of said detector array.

18. The method of claim 1 wherein the intensity of said light source is under control of said correction factor.

19. The method according to claim 18 further comprising the step of calibrating all sample measurement at said plural elements of said detector array.

* * * * *